United States Patent [19]

Pascoe

[11] Patent Number: 4,733,004

[45] Date of Patent: Mar. 22, 1988

[54] CONTINUOUS ESTERIFICATION OF METHACRYLIC ACID AND PRODUCT RECOVERY

[75] Inventor: Ralph F. Pascoe, Marysville, Ohio

[73] Assignee: Ashland Oil, Inc., Ashland, Ky.

[21] Appl. No.: 877,621

[22] Filed: Jun. 23, 1986

[51] Int. Cl.$^4$ ............................................. C07C 67/08
[52] U.S. Cl. .................................................. 560/205
[58] Field of Search ........................................ 560/205

[56] References Cited

U.S. PATENT DOCUMENTS

| | | | |
|---|---|---|---|
| 3,776,947 | 12/1973 | Shimizu et al. | 560/205 |
| 3,882,167 | 5/1975 | Lohmar et al. | 560/205 |
| 4,250,328 | 2/1981 | Fujita et al. | 560/218 |
| 4,435,594 | 3/1984 | Matsumura et al. | 560/205 |

OTHER PUBLICATIONS

Perry, John H., Chemical Engineers' Handbook, 4th Ed. (1963), McGraw Hill, Publ. at pp. 20–50.

Primary Examiner—Donald B. Moyer
Assistant Examiner—L. Hendriksen
Attorney, Agent, or Firm—John F. Jones

[57] ABSTRACT

A process for the esterification of an olefinically unsaturated carboxylic acid, such as methacrylic acid, with a lower alkanol, such as methanol, to form the corresponding ester over a solid cationic catalyst in which the carboxylic acid is used in excess of the alkanol on a molar basis, the improvement which comprises: (A) employing a hydraulically fluidized solid catalyst reactor for the continuous esterification reaction, (B) including in the esterification reaction a solvent which is a hydrocarbon having from 6 to 15 carbon atoms, (C) passing the effluent from the esterification reactor into a first distillation column in which the ester product and water by-product are taken overhead, (D) taking the unesterified carboxylic acid, solvent, and heavies from the bottom of the first distillation column, (E) separating the water from the ester in the overhead from (C) and recovering the ester product, (F) separating heavies from the carboxylic acid-solvent from (D) in a second distillation column, (G) recycling the carboxylic acid-solvent from (F) back to the esterification reactor (A), and (H) disposing of the heavies from (F) is described.

5 Claims, 1 Drawing Figure

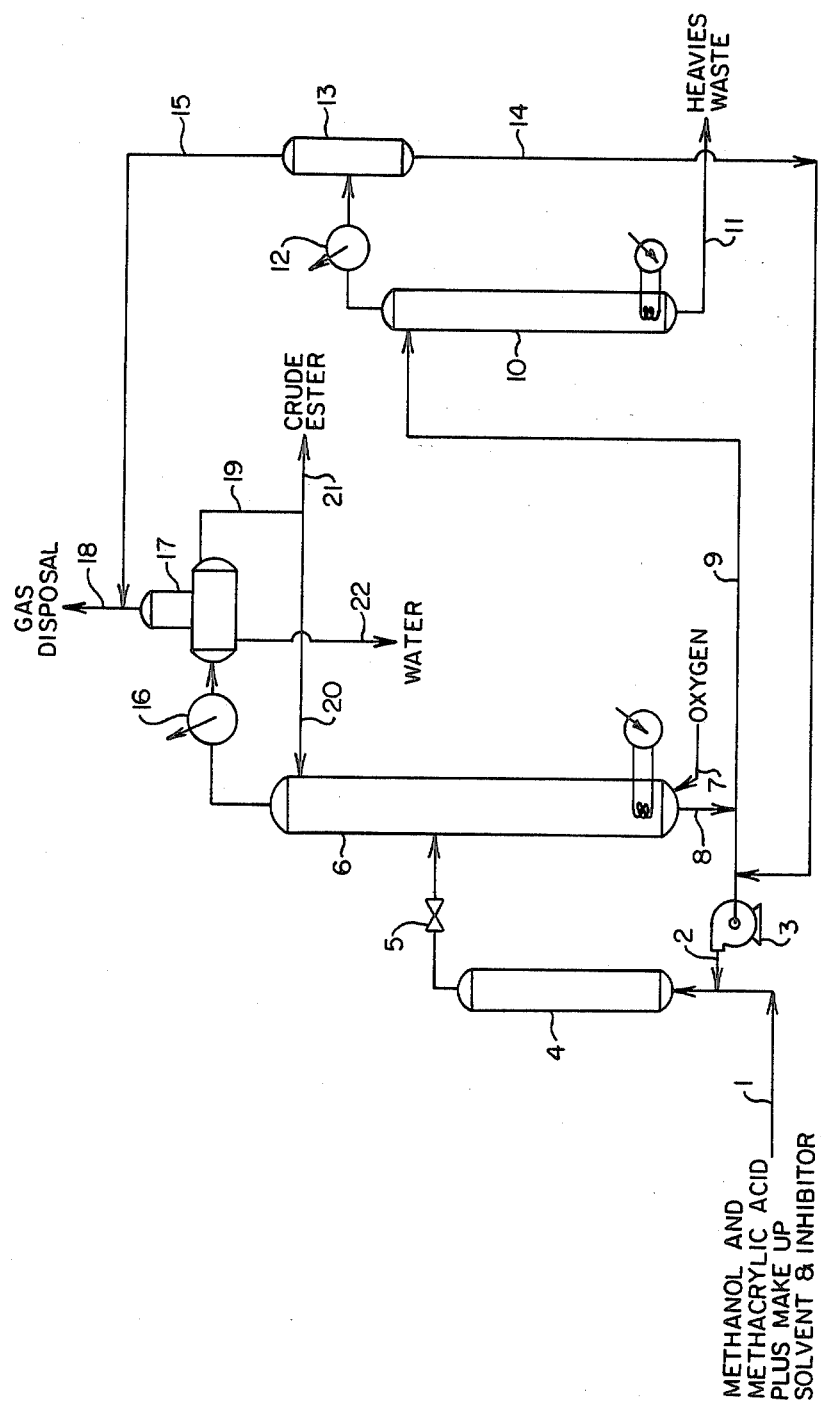

CONTINUOUS ESTERIFICATION OF METHACRYLIC ACID AND PRODUCT RECOVERY

This invention relates to a process for the esterification of methacrylic acid and to the recovery of the esterified product and more particularly pertains to an improved process for the esterification of methacrylic acid with a lower alkanol in the presence of a fluid bed solid cation exchange catalyst wherein the methacrylic acid is used in molar excess over the alkanol and wherein the surface of the solid catalyst is continuously washed free of polymer which forms thereon and to the recovery of the methacrylic acid ester product in high yield.

U.S. Pat. No. 3,639,460 describes an esterification reaction which can be practiced in a reactor using sulfuric acid as catalyst wherein the reaction products are concurrently separated from the reaction mixture as by distillation. The composition of the reaction mixture is also characterized in that alcohol is a limiting reactant in the reaction zone.

U.S. Pat. No. 4,250,328 discloses that ester product can be separated from the reaction mixture when the alcohol used in the esterification is present in small amounts (4%) in the product mixture.

Several patents disclose that esterification reactions can be catalyzed by strong acid cation exchange resins, e.g. U.S. Pat. Nos. 3,712,917, 3,776,947 and 4,250,328, for instance.

The use of sulfuric acid catalyst in the esterification reaction is undesirable in that it is corrosive and causes excessive and undesirable product losses associated with separation including removal of heavies from the catalyst.

The use of cation exchange resins as catalysts in the esterification reaction also has some drawbacks, particularly in the case in which the carboxylic acid used in the esterification is an olefinically unsaturated, readily polymerizable material such as methacrylic acid. When alcohol is used in excess in relation to the carboxylic acid to be esterified it is usually difficult to separate products from reactants because of the formation of numerous azeotropes among alcohol, acid and water mixtures. In the case in which alcohol is present as the limiting reactant, the amount of carboxylic acid reactant that must be present in order to drive the equilibrium reaction (alcohol plus carboxylic acid→carboxylic acid ester plus water) far to the right so as to avoid for the most part alcohol azeotropes, usually leads to the formation of some polymers which form on and agglomerate the cation exchange resin particles into an unusable mass in time. This fouling of the catalyst plus concomitant plugging of the reactor usually occurs within a few minutes to a few hours after start up and is a problem in both fixed bed and fluid bed catalyst systems.

I have discovered a process which will be more fully described below which provides means whereby the commercial advantages of using a cation exchange resin catalyst such as a polystyrene based sulfonic acid ion exchange resin and the like can be fully exploited in the production and recovery of methacrylic acid esters over long periods of reaction without the usual drawback of rapid and complete fouling, plugging and loss of activity of the catalyst.

I have discovered that lower alkanols, particularly methanol, act as effective solvents for removal of lower molecular weight methacrylic acid and possibly methacrylic acid ester polymers from the catalyst particles before they have aged and become insoluble. The embodiment of this discovery, concurrent with the requirement to react the alkanol as far toward extinction as possible, has been implemented by the use of a fluid bed esterification reactor employing a fluidized, particulate cation exchange resin catalyst wherein backmixing of the catalyst particles brings all of the catalyst particles into an alkanol rich section of the reactor during the reaction. The fluid bed also provides beneficial mild scrubbing action which favors solvation and removal of polymeric residues from the catalyst particles in the alkanol rich section of the process.

My discovery also embodies means to remove solvated polymer from the esterification reaction mixture after it is removed from the catalyst particles. This is accomplished by using a solvent which is compatible with the roles of polymer carrier, inhibitor solvent, esterification rate enchanger and efficient separations entrainer. Solvents of this type include decane, decalin and the like.

This invention is further illustrated in the accompanying drawings wherein an alcohol such as methanol and an unsaturated organic acid (methacrylic acid) and makeup solvent and inhibitor are fed singly or fed as a mixture shown as stream 1, to reactor unit 4. Stream 1 may also contain one or more additives including but not limited to make-up solvent and polymerization inhibitors. Recycled compounds shown as stream 2 are also fed to the reactor inlet after pressurizing with pump 3. Feeds to the reactor are preferentially introduced into the reactor as a single well mixed stream so as to simplify reactant mixing and dispersion witout the need to generate excessive turbulence in the reactor.

The feed rates for methanol and organic acid, stream 1, are near equimolar, and characterized by the adjustments necessary to cause the ratios of unreacted unsaturated organic acid in stream 1 and stream 2 to remain constant. The composition of stream 2 recycle is dominantly unsaturated organic acid and solvent and may range from 20% acid to 80% acid, but more usually will be near equal amounts of unsaturated carboxylic acid and solvent. Stream 2 may also contain small amounts of esters, alcohols, acids, inhibitors, dissolved air and water. A specific objective of stream 2 is to provide a large excess of unsaturated organic carboxylic acid with respect to the amount of methanol present so as to cause the equilibrium esterification reaction to proceed far toward completion. The beneficial consequences of this strategy are to minimize amounts of numerous azeotropic compositions with methanol and to eliminate the need for recovery and recycle of methanol and associated possible impurity accumulations. A detrimental consequence is the well known difficulty of handling readily polymerizable unsaturated organic acids at temperatures and conditions that strongly favor undesired polymerization.

The solvent present in the reaction mixture accomplishes a number of objectives in the process. Within the reactor such objectives include: inertness with respect to esterification reactions and to avoid other reactions which are not desirable; cause water formed in the reaction to phase separate by reduction of water solubility limit in the reaction mixture so as to favor equilibrium conversion; and act as a solvent for polymers formed in the normal operation of process equipment.

Reactor unit 4, is characterized as a hydraulically fluidized bed in which the extent of liquid back-mixing is minimized, but at the same time catalyst solids are mildly back-mixed so as to avoid severe mechanical impacts or abrasions that tend to prematurely degrade catalyst particles. The temperature of reaction will ordinarily be between 60° and 150° C., but preferably between 90° and 110° C. At the excessively higher temperatures various combinations of reactants and products can form low boiling azeotropes causing some vapors to be evolved. The formation of such vapors is not detrimental when present in amounts which do not disrupt or significantly upset the stability of desired fluidization process. The extent of such vapor formation can be suppressed by pressurization of the reactor. This is conveniently accomplished with feed and recycle pumps as well as a pressure control valve, unit 5.

The catalyst is characterized as a strong acid exchange resin as available from various manufacturers in various grades, formulations, size distributions and the like such as examples of catalysts used are not to be construed as a recommendation for a specific product nor is it to be construed as a limitation of the invention to such particular products. Catalyst is separated from the reaction mixture and retained in the reactor via screens, strainers, cyclones, filters, centrifuges or other such devices customarily known and used in solid-liquid separations, but preferably limited to devices that avoid severe particle to particle impact or abrasion that tends to degrade the catalyst. Means may also be provided such as well known and practiced in the prior art so as to continuously add catalyst and remove catalyst fragments or particulates formed or caused to be formed during the course of reaction.

A frequent and customary inhibitor well known in the art is hydroquinone, and various other hydroquinone derivatives may be used. The effectiveness of such inhibitors may be enhanced by the introduction of oxygen or air shown as stream 7. Such inhibitor can be introduced at a multiple number of locations including but not limited to raw material feed stream 1, and/or condensers where vapors are rich in polymerizable acids such as condenser 12.

The reaction mixture leaving reactor 4, through valve 5 is fed to a distillation column 6, wherein reaction products, especially ester and water are distilled overhead along with lesser amounts of unreacted methanol and controlled amounts of solvent selected according to ability to enhance heterogeneous azeotropy. The bottom product from column 6 as stream 8, is dominantly unsaturated organic acid and solvent. The main part of stream 8 is recycled to reactor 4 as stream 2. A lesser part of stream 8, usually less than 50%, and more commonly near and less than 10% is taken as side stream 9 to column 10 wherein the mixture of unsaturated organic acid and solvent and components more volatile than these are taken overhead in stripping action to leave heavy residues composed of polymers formed in the processing steps, inhibitors and the like. Heavy residues are removed from the process via stream 11. Vapors from column 10 are primarily condensed in unit 12 and the more volatile and uncondensed portions are phase separated from the liquids in unit 13. Liquids, now free of heavy residues are returned to the reaction as stream 14. The uncondensed fraction will ordinarily be very small in quantity and are sent to vent gas handling (Stream 18) via stream 15.

Those skilled in the art will recognize that certain design considerations are desirable for the combination of condenser 12 and phase separator 13, namely the need to introduce inhibitor, as well as a need for mild or gentle means to condense unsaturated organic acid such as a falling film condenser or similar equipment with associated pump around loops to maintain wetted surfaces.

A specific objective of this invention is to identify specific solvents that fulfill multiple purposes and objectives. One such objective is to minimize losses of unsaturated organic acids due to distillation and recovery operations in units 10 and 12. I have discovered that a solvent containing one or more components from the list of nonane, decane, trans-decalin and cis-decalin are particularly beneficial for this purpose. More specifically, the pressure condition for operation of column 10 can be selected so as to cause some solvent to be condensed at a slightly higher temperature than unsaturated organic acid so as to assure wetted condenser surfaces rich in solvent and dilute in acid, thus reducing risk of polymer formation. Concurrently, in the bottom of column 10 the choice of solvent component is such as to cause the unsaturated organic acid to be vaporized preferentially to solvent so as to permit more thorough stripping of monomeric acids and solvent from the heavy residues with reduced risk of additional polymer formation. Specifically, I have discovered that a solvent mixture of decane and cis-decalin satisfies these requirements over the whole practical operating range of column pressure, whereas, with decane alone the temperatures at the bottom of column 10 must be limited to values greater than 80° C. at a pressure of greater than 25 mmHg so as to avoid a domain where compositions in the last few trays of column 10 will be acid rich rather than solvent rich.

Returning now to the overhead stream from column 6, the vapors are condensed in unit 16 and phase separated in unit 17 to form a water rich layer, an organic rich layer and a non-condensible phase. The water rich layer is removed as stream 22 for further treatment, processing and/or disposal. The organic rich portion is composed of ester and solvent as well as very small amounts of methanol, organic acid and traces of moisture. This fraction is separated as stream 19 and is further divided into reflux stream 20 and product (methylmethacrylate or MMA) stream 21. Product stream 21 is removed for further separation, recovery and purification of ester and recycle of solvent and unsaturated organic acid. Such recycle components are reintroduced to reactor 4 preferentially via pump 3. The uncondensed, gaseous fraction from unit 17 are combined with stream 15 for disposal via Stream 18. The means for gaseous rejection will ordinarily be a vacuum device of sufficient capacity to maintain operating pressures on column 6 and column 10 at favorable levels, ordinarily less than 760 mm/Hg and more usually near 100 mm/Hg or less.

A specific objective of the invention is to provide a solvent mixture that satisfies multiple objectives. One such objective is to facilitate the phase separation of aqueous and organic components in unit 17. Solvent components favored for this function are selected from hydrocarbons in the C6 to C15 range either as pure components or as a refinery stream. particularly beneficial components are decane, decalin, heptane and octane and the like so as to combine inertness, low mutual solubility with aqueous phase for heterogeneous azeotropy, favorable water carrying capacity and at the same time avoid higher pressures that otherwise would be needed in reactor 4 if lower molecular weight hydrocarbons from azeotropes with unreacted methanol. Decane and decalin are the preferred solvent components in this invention.

The reflux ratio of mixed solvent and ester should be sufficient to prevent more than trace amounts of unsaturated organic acid from appearing in the overhead product.

I claim:

1. In the process for the esterification of methacrylic acid with a lower alkanol to form the corresponding ester over a solid cationic catalyst in which the methacrylic acid is used in excess of the alkanol on a molar basis, the improvement which comprises carrying out the process at a temperature in the range of from 60° to 150° C. and:

(A) employing a hydraulically fluidized solid catalyst reactor for the continuous esterification reaction, (B) including in the esterification reaction a solvent which is a hydrocarbon having from 6 to 15 carbon atoms, (C) passing the effluent from the esterification reactor into a first distillation column in which the ester and water by-product are taken overhead, (D) taking the unesterified methacrylic acid, solvent, and heavy residues from the bottom of the first distillation column, (E) separating the water from the ester overhead from (C) and recovering the ester product, (F) separating heavy residues from the methacrylic acid-solvent from (D) in a second distillation column, (G) recycling the methacrylic acid-solvent from (F) back to the esterification reactor (A), and (H) disposing of the heavy residues from (F).

2. The process of claim 1 wherein the cationic catalyst is a particulate cation exchange resin.

3. The process of claim 2 wherein the lower alkanol is methanol.

4. The process of claim 3 wherein the solvent is decane, decalin or mixtures thereof.

5. The process of claim 4 wherein the particulate cation exchange resin is a polystyrene based sulfonic acid ion exchange resin.

* * * * *